(12) United States Patent
Kulseth et al.

(10) Patent No.: US 6,806,045 B2
(45) Date of Patent: Oct. 19, 2004

(54) METHOD FOR THE IDENTIFICATION OF A RECEPTOR

(75) Inventors: Mari Ann Kulseth, Oslo (NO); Dagfinn Lovhaug, Oslo (NO); Aslak Godal, Oslo (NO)

(73) Assignee: Amersham Health AS, Oslo (NO)

( * ) Notice: Subject to any disclaimer, the term of this patent is extended or adjusted under 35 U.S.C. 154(b) by 0 days.

(21) Appl. No.: 10/052,299

(22) Filed: Jan. 18, 2002

(65) Prior Publication Data

US 2002/0106643 A1 Aug. 8, 2002

Related U.S. Application Data

(63) Continuation of application No. PCT/NO00/00245, filed on Jul. 20, 2000.
(60) Provisional application No. 60/146,865, filed on Aug. 3, 1999.

(30) Foreign Application Priority Data

Jul. 21, 1999 (GB) ................................................ 9917111

(51) Int. Cl.⁷ ............................ C12Q 1/70; C12P 21/06; C12N 15/00

(52) U.S. Cl. .................................. 435/5; 435/6; 435/7.2; 435/7.8; 435/69.1; 435/70.1; 435/325

(58) Field of Search ............................. 435/235.1, 325, 435/320.1, 69.1, 5, 6, 7.2, 7.8, 70.1

(56) References Cited

FOREIGN PATENT DOCUMENTS

| WO | WO 98/18500 A2 | 5/1998 |
|---|---|---|
| WO | WO 99/55837 A2 | 11/1999 |

*Primary Examiner*—Hankyel T. Park
(74) *Attorney, Agent, or Firm*—Robert F. Chisholm; Li Cai

(57) ABSTRACT

A method for the identification and characterization of a receptor in target tissue for which a selected vector has affinity, wherein a transfected cell line expressing the receptor is added to a suspension of encapsulated microbubbles to which the selected vector is coupled and allowing the microbubbles and cells coupled thereto to float to the surface of the suspension. Upon isolating the microbubble-bound cells at the surface, these may be cultured to study the receptor, or cells may be lysed, amplifying the receptor-encoding cDNA and sequencing the cDNA.

9 Claims, No Drawings

METHOD FOR THE IDENTIFICATION OF A RECEPTOR

This application is a continuation application of international application No. PCT/NO00/00245 filed Jul. 20, 2000, the entire disclosure of which is hereby incorporated by reference.

This application claims benefits of U.S. Provisional application 60/146,865 filed Aug. 3, 1999.

This invention relates to the identification and investigation of receptors having affinity for selected vectors.

It is well known that particular biological receptors such as cell receptors may bind certain vectors, also known as ligands or binding partners, often with a high degree of specificity. Considerable attention is currently being given to the preparation of synthetic peptides and other vectors which target disease-specific markers in vivo, for example as potential components of targeted imaging agents and/or therapeutic agents. Once a vector is found to have appropriate targeting properties, for example affinity for endothelial or other target tissue, it is desirable to identify the receptor to which it is binding.

The present invention is based on the finding that receptor identification may be achieved relatively quickly, simply and cheaply using a retroviral cDNA library containing activated genes from the target tissue to transfect an appropriate cell line and separating cells which express the receptor of interest using encapsulated gas microbubbles which are coupled to the vector under investigation. The cDNA encoding this receptor may then be amplified, e.g. using the polymerase chain reaction, and identified, for example by sequencing and comparison of the sequence with sequences in a database e.g. of known genes.

The fact that a wide range of vectors may be bound to microbubbles is a very important advantage of the invention.

Mammalian cells transfected with retroviral cDNA libraries have previously been employed in a variety of identification techniques primarily based on phenotypical changes of cells caused by the transfected gene. For example, Nicholson et al. in *J. Leukoc. Biol.* 63(6), pp. 665–668 (1998) describe the identification of a new family of negative regulators of signal transduction by selecting cells that were no longer able to differentiate in response to interleukin-6. Cell surface molecules have been identified through the transfection of a cell line with a cDNA retroviral library; thus Tailor et al. in *J. Virol.* 73(5), pp. 4470–4474 (1999) describe the identification of a cell surface receptor for type D simian viruses after retroviral transfection using human T-lymphocyte cDNA.

Zannettino et al. in *J. Immunol.* 156(2), pp. 611–620 (1996) describe a method for rapidly isolating genes encoding cell surface molecules from a human bone marrow stromal cell cDNA library constructed in a retroviral vector. A selection strategy using antibody (e.g. monoclonal antibody)-coated magnetic beads is employed to isolate cells expressing particular cell surface antigens; cDNA encoding the selected cell surface molecules is recovered using the polymerase chain reaction and is subjected to sequencing.

Separation of cells using magnetic beads, e.g. antibody-coated superparamagnetic polymer particles such as Dynabeads®, suffers from a number of disadvantages. Firstly, when a magnetic field is applied to a sample, magnetic beads and target cell/bead complexes will rapidly be drawn through the sample towards the magnet. Since beads such as polymer particles are hard and may typically be of similar size to cells, this rapid movement can cause significant damage to target cells in the sample.

Moreover, detachment of separated cells from the beads can be a difficult and time-consuming process. A representative technique where the beads are coated with a monoclonal antibody having specificity for the target cells involves use of a polyclonal antibody that reacts with Fab-fragments of monoclonal antibodies to effect direct dissociation of the antigen-antibody binding between the beads and the target cells. This technique is only suitable for use with certain types of polymer particle and certain monoclonal antibodies. Alternative detachment methods include overnight incubation at 37° C., enzymatic cleavage and the introduction of reagents which compete for the same target as the beads.

Due to the complicated nature of these detachment techniques, magnetic beads are predominantly employed in "negative" component separations, i.e. processes in which unwanted components are bound to the magnetic beads and isolated, leaving the desired components in the sample. Their use in "positive" selections where a specific component is targeted and isolated, as in the procedure of Zannettino et al., is comparatively limited.

Gentle positive selection is important when the cells expressing the particular receptor are going to be withdrawn for further growth. Flotation separations as used in accordance with the present invention, in which cells expressing the receptor of interest become bound to vectors coupled to surfaces of encapsulated gas microbubbles, have the advantage that the efficiency of such separations is enhanced by the substantial density difference between gas microbubbles and liquid sample media, so that the process is capable of high sensitivity. Flotation separations inherently proceed more gently than magnetic separations and the gas microbubbles may advantageously be prepared using flexible encapsulating materials, so that the possibility of causing damage to sensitive cells during separation may thus be minimised. The use of encapsulated gas microbubbles also permits ready removal of the microbubbles from the cells after separation, simply by bursting the microbubbles. This is of particular advantage in a positive selection process, and encapsulated microbubbles coupled to a wide range of vectors may be used in the process of the invention; it is therefore far more widely applicable than the procedure of Zannettino et al., which is limited to the use of antibodies as vectors.

SUMMARY OF THE INVENTION

Thus according to one aspect of the invention there is provided a method for the identification of a receptor in target tissue for which a selected vector has affinity, said method comprising:

i) creating retroviral particles containing a library of mRNA from the target tissue;

ii) transfecting a non-adherent cell line which does not bind with the selected vector by infecting the cells with said retroviral particles;

iii) adding to the transfected cell line a suspension of encapsulated microbubbles to which the selected vector is coupled and allowing the microbubbles and cells coupled thereto to float to the surface of the suspension;

iv) isolating the microbubble-bound cells at the surface;

v) lysing the isolated cells, amplifying the receptor-encoding cDNA therefrom and sequencing said cDNA; and optionally vi) comparing the thus-obtained cDNA sequence data with gene bank sequence data.

In an alternative embodiment there is provided a method for the investigation of a receptor as defined above in which the isolated cells from step (iv) are cultured, rather than lysed, to allow further study of the nature of the receptor to take place, e.g. studies on affinity between the isolated cells and potential vectors.

DETAILED DESCRIPTION OF THE INVENTION

Representative investigations on the nature of receptors include, for example, investigations on interactions with or affinities to vectors or similar molecules, such as ligand molecules.

Vectors which may be used in the process of the invention include peptides, proteins (e.g. antibodies), nucleotides, hormones, growth factors, cytokines, carbohydrates, lipids, therapeutic agents (including drugs which act through receptor-mediated cell entry) etc.

The target tissue may, for example, be endothelial, myocardial or tumour tissue. Representative target tissue cell types include all CD positive cells such as antigen presenting cells (e.g. Langerhans cells, endothelial cells, trophoblasts, neural cells and epithelial cells, including epithelial tumour cells which are markers of cancer not otherwise found in blood), hematopoietic cells (e.g. lymphocytes, granulocytes, monocytes, macrophages, reticulocytes, erythrocytes, megakaryocytes, NK cells and platelets), hematopoietic progenitor cells, and other cells expressing the transferring receptor etc.

Equipment for preparing retroviral libraries is available from Clontech Laboratories, Inc. (Palo Alto, Calif.). In general, mRNA from activated or inactivated target cells (e.g. endothelial cells) is isolated, cDNA is synthesised therefrom and is ligated into a retroviral vector. This is transfected into a packaging cell line to produce infectious, replication-incompetent retroviral particles which contain a library of mRNA from the target cells.

The cell line to be transfected with the retroviral particles should preferably be capable of growth in suspension. Representative examples include monoblast cell lines; other suitable cell lines may readily be determined by the skilled artisan. Infection of mammalian cells by retroviral particles is a powerful technique for the introduction of genes into such cells; the transducing level may be up to 100%. The transfection is regarded as stable in that transfected genetic material is incorporated in the genome of the cell; the transfected cells may be frozen and stored, with portions being used in a number of experiments. In the case of endothelial cell lines the transfected cells will express endothelial specific genes and endothelial receptors will be located at the surfaces of the transfected cells.

Encapsulated microbubbles which may be useful in the process of the invention include any stabilised microbubbles which may be coupled to the selected vector. Representative examples of microbubbles include those which are suitable for use in targetable contrast agent formulations, especially targetable ultrasound contrast agent formulations, and include microbubbles of gas stabilised (e.g. at least partially encapsulated) by a coalescence-resistant surface membrane (for example gelatin, e.g. as described in WO-A-8002365), a filmogenic protein (for example an albumin such as human serum albumin, e.g. as described in U.S. Pat. No. 4,718,433, U.S. Pat. No. 4,774,958, U.S. Pat. No. 4,844,882, EP-A-0359246, WO-A-9112823, WO-A-9205806, WO-A-9217213, WO-A-9406477, WO-A-9501187 or WO-A-9638180) or protein as described in WO-A-9501187 or WO-A-9746264, a polymer material (for example a synthetic biodegradable polymer as described in EP-A-0398935, a synthetic polymer as described in U.S. Pat. No. 5,611,344, a modified polymer as described in WO-A-9402106, an elastic interfacial synthetic polymer membrane as described in EP-A-0458745, a microparticulate biodegradable polyaldehyde as described in EP-A-0441468, a microparticulate N-dicarboxylic acid derivative of a polyamino acid—polycyclic imide as described in EP-A-0458079, or a biodegradable polymer as described in WO-A-9317718 or WO-A-9607434), a lipid, protein or polymer material as described in WO-A-9640285 or WO-A-9748337, a non-polymeric and non-polymerisable wall-forming material (for example as described in WO-A-9521631), or a surfactant (for example a polyoxyethylene-polyoxypropylene block copolymer surfactant such as a Pluronic, a polymer surfactant as described in WO-A-9506518, a film-forming surfactant such as a phospholipid, e.g. as described in WO-A-9211873, WO-A-9217212, WO-A-9222247, WO-A-9409829, WO-A-9428780, WO-A-9503835 or WO-A-9729783, or by a surfactant from the extensive list contained in EP-A-0727225 or as described in WO-A-9416739, a lipid as describe in WO-A-9428874 or WO-A-9428873, a lyophilised lipid as described in WO-A-9740858, a pressure resistant barrier forming material as described in WO-A-9640283, a fluorine containing amphiphilic material as in WO-A-9604018 or one or more lipopeptides). The contents of the various publications referred to above are incorporated herein by reference. Hollow inorganic microparticles, for example comprising calcium carbonate, quartz, alumina, nickel hydroxide or ferric hydroxide, may also be useful.

In one preferred embodiment of the invention, the encapsulating material comprises one or more phospholipids and/or lipopeptides. Thus, not only do gas microbubbles encapsulated by such materials tend to exhibit particularly high stability, but their molecules normally contain reactive moieties onto which vectors such as antibodies or other affinity ligands may be attached, e.g. through an appropriate linking group.

Representative examples of useful phospholipids include lecithins (i.e. phosphatidylcholines), for example natural lecithins such as egg yolk lecithin or soya bean lecithin and synthetic or semisynthetic lecithins such as dimyristoylphosphatidylcholine, dipalmitoylphosphatidylcholine or distearoyl-phosphatidylcholine; phosphatidic acids; phosphatidylethanolamines; phosphatidylserines including saturated (e.g. hydrogenated or synthetic) natural phosphatidylserine and synthetic or semisynthetic dialkanoylphosphatidylserines such as distearoylphosphatidylserine, dipalmitoylphosphatidylserine and diarachidoylphospahtidylserine; phosphatidylglycerols; phosphatidylinositols; cardiolipins; sphingomyelins; fluorinated analogues of any of the foregoing; mixtures of any of the foregoing and mixtures with other lipids such as cholesterol.

A more detailed discussion of phospholipids useful for stabilising gas microbubbles is contained in WO-A-9729783, the contents of which are incorporated herein by reference.

Lipopeptides which may be used include lipid-substituted peptide moieties which are amphiphilic and capable of membrane formation. Such lipopeptides may be formed from individual peptide units each comprising from 2 to 50 amino acid residues and each carrying one or more lipophilic hydrocarbon chains containing between 5 and about 50 carbon atoms.

The number of amino acid residues in the individual peptide units is preferably less than 20, more preferably less than 10, and most preferably between 2 and 8. Clearly, keeping the number of amino acid residues to a minimum will both reduce costs and allow easier preparation of the lipopeptides.

In principle, any amino acid residues may be used in the preparation of individual peptide units, provided that the end product lipopeptide is amphiphilic. In a preferred embodiment, however, the peptide units comprise residues of the readily available twenty naturally occurring essential amino acids.

In one embodiment the peptide units may comprise alternating hydrophobic and hydrophilic amino acid residues such as alanyl and diaminopropionyl, and may comprise one or more complementary sequences and/or a targeting sequence with affinity for biological receptors. In a preferred embodiment, residues of charged amino acids such as lysine and glutamic acid are selected to provide side-chain functionalities comprising positively and/or negatively charged groups respectively at neutral pH. Although not wishing to be limited by theory, it is envisaged that these charged groups may help in stabilisation of the outer parts of membranes by forming ion-pairs or salt bridges. The alignment of oppositely charged groups leading to membrane stability is possible only if the peptide sequences involved are complementary to one another.

The lipid substituent of the lipopeptides preferably comprises an alkyl, alkenyl or alkynyl chain, especially an alkyl chain. Such chains preferably contain between 5 and 25 carbon atoms and most preferably are obtainable from readily available fatty acid derivatives. Suitable fatty acids include oleic acid, stearic acid, palmitic acid and the like; such fatty acids are well-known to the person skilled in the art. The number of hydrocarbon chains per individual lipopeptide unit may vary depending on the number of residues present and may readily be determined by the person skilled in the art; typically each lipopeptide molecule will comprise one or two hydrocarbon chains.

The use of gas microbubbles in which the encapsulating membranes bear a net overall charge, for example owing to the presence of charged stabilising materials such as appropriate phospholipids or lipopeptides, may be advantageous in terms of enhancing the stability and dispersibility of the microbubbles, as well as their resistance to coalescence, thereby avoiding the need to use stabilising additives.

Membrane-forming amphiphilic encapsulating materials such as phospholipids and lipopeptides may be present at the microbubble-suspending liquid interfaces as monolayers, bilayers or multilayers (e.g. comprising a plurality of bilayers).

In principle any substances, including mixtures, which are at least partially, e.g. substantially or completely, in gaseous or vapour form at typical processing temperatures (e.g. approximately 20° C.) may be used as the microbubble gas, the use of biocompatible gases being preferred. Representative gases thus include air; nitrogen; oxygen; carbon dioxide; hydrogen; inert gases such as helium, argon, xenon or krypton; sulphur fluorides such as sulphur hexafluoride, disulphur decafluoride or trifluoromethylsulphur pentafluoride; selenium hexafluoride; optionally halogenated silanes such as methylsilane or dimethylsilane; low molecular weight hydrocarbons (e.g. containing up to 7 carbon atoms), for example alkanes such as methane, ethane, a propane, a butane or a pentane, cycloalkanes such as cyclopropane, cyclobutane or cyclopentane, alkenes such as ethylene, propene, propadiene or a butene, and alkynes such as acetylene or propyne; ethers such as dimethyl ether; ketones; esters; halogenated low molecular weight hydrocarbons (e.g. containing up to 7 carbon atoms); and mixtures of any of the foregoing. Advantageously at least some of the halogen atoms in halogenated gases are fluorine atoms; thus biocompatible halogenated hydrocarbon gases may, for example, be selected from bromochlorodifluoromethane, chlorodifluoromethane, dichlorodifluoromethane, bromotrifluoromethane, chlorotrifluoromethane, chloropentafluoroethane, dichlorotetrafluoroethane, chlorotrifluoroethylene, fluoroethylene, ethylfluoride, 1,1-difluoroethane and perfluorocarbons. Representative perfluorocarbons include perfluoroalkanes such as perfluoromethane, perfluoroethane, perfluoropropanes, perfluorobutanes (e.g. perfluoro-n-butane, optionally in admixture with other isomers such as perfluoroiso-butane), perfluoropentanes, perfluorohexanes or perfluoroheptanes; perfluoroalkenes such as perfluoropropene, perfluorobutenes (e.g. perfluorobut-2-ene), perfluorobutadiene, perfluoropentenes (e.g. perfluoropent-1-ene) or perfluoro-4-methylpent-2-ene; perfluoroalkynes such as perfluorobut-2-yne; and perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane or perfluorocycloheptane. Other halogenated gases include methyl chloride, fluorinated (e.g. perfluorinated) ketones such as perfluoroacetone and fluorinated (e.g. perfluorinated) ethers such as perfluorodiethyl ether. The use of perfluorinated gases, for example sulphur hexafluoride and perfluorocarbons such as perfluoropropane, perfluorobutanes, perfluoropentanes and perfluorohexanes, may be particularly advantageous in view of the recognised high stability of microbubbles containing such gases. Other gases with physicochemical characteristics which cause them to form highly stable microbubbles may likewise be useful. It will be appreciated that gases from the above list which boil above the intended separation processing temperature will in general be employed as components of mixtures with other more volatile gases rather than be used alone.

The microbubbles may conveniently be of similar size to the transfected cells; thus, for example, the microbubbles may have diameters of 1 to 10 μm, preferably 3 to 5 μm. They may be coupled to the selected vector either directly or through appropriate linking groups. Coupling may be achieved by covalent or non-covalent means, for example involving interaction with one or more functional groups located on the microbubble and/or vector. Examples of chemically reactive functional groups which may be employed for this purpose include amino, hydroxyl, sulfhydryl, carboxyl, and carbonyl groups, as well as carbohydrate groups, vicinal diols, thioethers, 2-aminoalcohols, 2-aminothiols, guanidinyl groups, imidazolyl groups and phenolic groups. Coupling of the vector and microbubble, optionally via a linker, may therefore be readily achieved using routine techniques, for example as summarised in WO-A-9818501, the contents of which are incorporated herein by reference.

The rate at which microbubbles and coupled cells float to the surface of the suspension may, if desired, be increased by subjecting the suspension to centrifugation using appropriate (e.g. conventional) centrifugation apparatus.

Floating microbubble-bound cells may be isolated by, for example, decanting, sucking or skimming off the floating microbubble layer, whereafter both bound and unbound microbubbles may be removed, e.g. by bursting.

Alternatively, flow cytometry or other cell-picking techniques may be used to isolate floated cells on an individual basis.

The isolated microbubble-bound transfected cells may be useful for a number of studies, for example studies of affinity between the receptor-carrying cells and potential vectors. Such affinities between vectors and receptors play an important role in a variety of diseases involving mechanisms such as interaction with ligand molecules, drugs, second messengers and infectious agents; activation, sensitization and desensitization; cell entry (for example of drugs), uptake and transport; and other receptor-mediated cell-cell or cell-ligand interactions.

In cases where it is desired to remove microbubbles by bursting this may be done before or after culturing of the cells and it may, for example, be effected by transient application of an overpressure or underpressure, by ultrasonication or by pH change. Tests have shown that brief overpressures of up to 2-4 atmospheres may be used to destroy microbubbles without harming cells. Following bursting, a proportion of microbubble encapsulating material may remain attached to the cells, but this will generally be insufficient to affect their viability.

Following their isolation the floated cells may be lysed, e.g. in per se known manner, and the cDNA which encodes the receptor for the selected vector may be amplified, preferably by means of the polymerase chain reaction. The nucleotide sequence of the amplified cDNA may be determined, e.g. in per se known manner; comparison of the thus-obtained sequence data with gene bank sequence data allows the identity of the receptor to be determined.

The following non-limitative Example serves to illustrate the invention.

EXAMPLE a) A retroviral library is created using the Retro-X™ System from ClonTech Laboratories (Palo Alto, Calif.—see User manual PT3132-1). mRNA is isolated from endothelial cells and cDNA synthesised therefrom is ligated into the retroviral vector pLNCX (ClonTech). Transfection into the RetroPak™ PT67 packaging cell line (ClonTech) generates infectious replication-incompetent retroviral particles containing a library of endothelial mRNA.

b) U937-1 cells are grown in RPMI-1640 medium containing 10% fetal calf serum, 2 mM L-glutamine and antibiotic, and are infected with the retroviral particles from (a) above, as described in the ClonTech User manual PT3230-1 (Retroviral cDNA library).

c) A suspension of perfluorobutane microbubbles encapsulated with distearoylphosphatidylserine doped with a lipopeptide comprising an endothelial specific peptide, emerged after phage display biopanning, is added to the transfected cells from (b) above in a centrifuge tube, the microbubbles and cells being in the ratio 10:1. The tube is placed on a roller mixer and maintained for 37° C. for 30 minutes, whereafter it is centrifuged for 5 minutes at 200×g. Floated microbubble-bound cells are isolated e.g. by flow cytometry.

d) The isolated cells from (c) above are lysed and the cDNA encoding the peptide receptor is amplified by a polymerase chain reaction using the primers provided with the pLNCX retroviral vector. The nucleotide sequence of the amplified cDNA is determined using an ABI Prism BigDye Terminator Cycle Sequencing Ready Reaction kit (Perkin Elmer) and the obtained sequence data is compared to sequences in the EMBL/Genbank in order to identify the receptor.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A method for the identification and investigation of a receptor in target tissue for which a selected vector has affinity, said method comprising:
   i) creating retroviral particles containing a library of mRNA from the targe tissue;
   ii) transfecting a non-adherent cell line which does not bind with the selected vector by infecting the cells with said retroviral particles;
   iii) adding to the transfected cell line a suspension of encapsulated gas microbubbles to which the selected vector is coupled and allowing the microbubbles and cells coupled thereto to float to the surface of the suspension;
   iv) isolating the microbubble-bound cells at the surface; and either
   v-a) lysing the isolated cells, amplifying the receptor-encoding cDNA therefrom and sequencing said cDNA; and optionally
   v-b) comparing the thus-obtained sequence data with gene bank sequence data; or
   vi-a) culturing the isolated cells; and
   vi-b) investigating affinities of vectors to the isolated cells.

2. The method according to claim 1 wherein said vector is selected from peptides, proteins, antibodies, nucleotides, hormones, growth factors, cytokines, carbohydrates, lipids, therapeutic agents and drugs acting through receptor-mediated cell entry.

3. The method according to claim 1 wherein the encapsulated microbubbles of step iii) are selected from microbubbles of gas stabilised by a coalescence-resistant surface membrane, a filmogenic protein, a polymer material, a lipid, a non-polymeric and non-polymerisable wall-forming material and a surfactant.

4. The method according to claim 3 wherein said surfactant is selected from one or more phospholipids and one or more lipopeptides.

5. The method according to claim 1 wherein said gas is a biocompatible gas or gas mixture selected from perfluorinated gases, preferably from sulphur hexafluoride, perfluoropropane, perfluorobutanes, perfluoropentanes and perfluorohexanes.

6. The method according to claim 1 wherein said is perfluorobutane and said surfactant is phosphatidylserine.

7. The method according to claim 1 wherein the microbubbles are removed before or after culturing, said removal is effected by bursting with a technique selected from ultrasonication, pH change or transient application of overpressure or underpressure.

8. Microbubble-bound transfected cells producible by method steps i) to iv) of claim 1.

9. Microbubble-bound transfected cells according to claim 8 wherein the microbubbles are of similar size to the transfected cells, preferably the microbubbles have diameters of 1 to 10 $\mu$m, more preferably 3 to 5 $\mu$m.

* * * * *